United States Patent
Wunberg et al.

(10) Patent No.: US 7,662,822 B2
(45) Date of Patent: Feb. 16, 2010

(54) SUBSTITUTED AZAQUINAZOLINES HAVING AN ANTIVIRAL ACTION

(75) Inventors: Tobias Wunberg, Hinterbrühl (AT); Judith Baumeister, Melchelen (BE); Mario Jeske, Solingen (DE); Frank Süßmeier, Wuppertal (DE); Holger Zimmermann, Wuppertal (DE); Kerstin Henninger, Wuppertal (DE); Dieter Lang, Velbert (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 101 days.

(21) Appl. No.: 11/579,919

(22) PCT Filed: Apr. 23, 2005

(86) PCT No.: PCT/EP2005/004384

§ 371 (c)(1),
(2), (4) Date: Nov. 29, 2007

(87) PCT Pub. No.: WO2005/113552

PCT Pub. Date: Dec. 1, 2005

(65) Prior Publication Data

US 2008/0132515 A1 Jun. 5, 2008

(30) Foreign Application Priority Data

May 7, 2004 (DE) .................. 10 2004 022 672

(51) Int. Cl.
*C07D 471/04* (2006.01)
*A61K 31/497* (2006.01)
*C07D 213/75* (2006.01)
*C07D 213/73* (2006.01)
*C07F 9/06* (2006.01)
*C07F 9/28* (2006.01)
*C07C 265/12* (2006.01)
*A61P 31/12* (2006.01)

(52) U.S. Cl. .................. 514/252.16; 544/279; 546/309; 546/311; 546/22; 546/306; 560/358

(58) Field of Classification Search ............ 514/264.11, 514/252.16; 544/279
See application file for complete search history.

(56) References Cited

U.S. PATENT DOCUMENTS

2002/0019397 A1  2/2002  Schnute et al. .............. 514/243
2005/0065160 A1  3/2005  Wunberg et al. ....... 514/252.17

FOREIGN PATENT DOCUMENTS

| EP | 1201765 | 2/2002 |
| WO | 2004072048 | 8/2004 |
| WO | 2004096778 | 11/2004 |
| WO | 2004099212 | 11/2004 |

OTHER PUBLICATIONS

Viral Defense Found., <http://www.viraldefense.org/mission.htm>, downloaded Oct. 21, 2008.*
Visiting Nurse Assns. of America, <http://www.vnaa.org/vnaa/gen/Germ_Protection_Center_Cold_and_Flu_Resources>, downloaded Oct. 21, 2008.*
Lischka, et al., Current Opinion in Pharmacology (Article in Press, Corrected Proof), 2008, 8:1-8.*
Griesser, Chapter 8, The Importance of Solvates (pp. 211-230), in the text, Polymorphism: In the Pharmaceutical Industry, Hilfiker, 2006.*
Wikipedia, Maribavir, updated Feb. 10, 2009, <http://en.wikipedia.org/wiki/Maribavir>, downloaded Mar. 10, 2009.*
Saito, et al., A Facile and Efficient Carbodiimide-Mediated Synthesis of Dihydroquinazolines via a Tandem Nucleophilic Addition-Intramolecular Hetero Conjugate Addition Annulation Strategy, Tet. Lets., 37(2): 209-212 (1996).
Wang & Hauske, Solid-Phase Synthesis of 3,4-Dihydroquinazoline, Tet. Lets., 38(50): 8651-8654 (1997).

* cited by examiner

*Primary Examiner*—Mark L Berch
*Assistant Examiner*—Cecilia M Jaisle
(74) *Attorney, Agent, or Firm*—Edwards Angell Palmer & Dodge LLP; Nicholas J. DiCiglie, Jr.

(57) ABSTRACT

This invention relates to substituted azaquinazolines, to a process for their preparation, to pharmaceutical compositions containing them, and to their use for the treatment and/or prophylaxis of diseases, especially for use as antiviral agents, in particular against cytomegaloviruses.

5 Claims, No Drawings

SUBSTITUTED AZAQUINAZOLINES HAVING AN ANTIVIRAL ACTION

The invention relates to substituted-azaquinazolines and process for their preparation, and to their use for producing medicaments for the treatment and/or prophylaxis of diseases, especially for use as antiviral agents, in particular against cytomegaloviruses.

The synthesis of dihydroquinazolines is described in Saito T., et al. *Tetrahedron Lett.*, 1996, 37, 209-212 and in Wang F., et al. *Tetrahedron Lett.*, 1997, 38, 8651-8654.

Although agents having antiviral activity and different structures are available on the market, the therapies currently available with ganciclovir, valganciclovir, foscarnet and cidofovir are associated with severe side effects, e.g. nephrotoxicity, neutropenia or thrombocytopenia. It is moreover regularly possible for a resistance to develop. Novel agents for effective therapy are therefore desirable.

One object of the present invention is therefore to provide novel compounds with identical or improved antiviral effect for the treatment of viral infectious diseases in humans and animals.

It has surprisingly been found that the substituted azaquinazolines described in the present invention have antiviral activity.

The invention relates to compounds of the formula

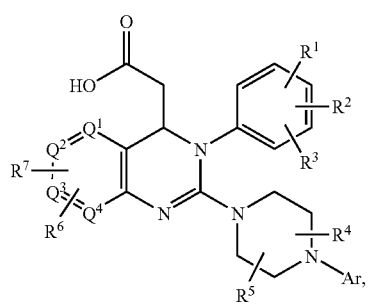

(I)

in which

Ar is aryl, in which aryl may be substituted by 1 to 3 substituents, where the substituents are selected independently of one another from the group consisting of alkyl, alkoxy, formyl, hydroxycarbonyl, alkylcarbonyl, alkoxycarbonyl, trifluoromethyl, halogen, cyano, hydroxy, amino, alkylamino, aminocarbonyl and nitro, in which alkyl may be substituted by 1 to 3 substituents, where the substituents are selected independently of one another from the group consisting of halogen, amino, alkylamino, hydroxy and aryl, or two of the substituents on the aryl form together with the carbon atoms to which they are bonded a 1,3-dioxolane, a cyclopentane ring or a cyclohexane ring, and an optionally present third substituent is selected independently thereof from the said group, $Q^1$, $Q^2$, $Q^3$ and $Q^4$ are CH or N, where one or two of $Q^1$, $Q^2$, $Q^3$ and $Q^4$ are N and the others are simultaneously CH, $R^1$ is hydrogen, amino, alkyl, alkoxy, alkylamino, alkylthio, cyano, halogen, nitro or trifluoromethyl, $R^2$ is hydrogen, alkyl, alkoxy, alkylthio, cyano, halogen, nitro or trifluoromethyl, $R^3$ is amino, alkyl, alkoxy, alkylamino, alkylthio, cyano, halogen, nitro, trifluoromethyl, alkyl-sulphonyl or alkylaminosulphonyl, or one of the radicals $R^1$, $R^2$ and $R^3$ is hydrogen, alkyl, alkoxy, cyano, halogen, nitro or trifluoromethyl, and the other two form together with the carbon atoms to which they are bonded a 1,3-dioxolane, a cyclopentane ring or a cyclohexane ring, $R^4$ is hydrogen or alkyl, $R^5$ is hydrogen or alkyl, or the radicals $R^4$ and $R^5$ in the piperazine ring are bonded to exactly opposite carbon atoms and form a methylene bridge optionally substituted by 1 to 2 methyl groups, $R^6$ is hydrogen, alkyl, alkoxy, alkylthio, formyl, hydroxycarbonyl, aminocarbonyl, alkyl-carbonyl, alkoxycarbonyl, trifluoromethyl, halogen, cyano, hydroxy or nitro, and $R^7$ is hydrogen, alkyl, alkoxy, alkylthio, formyl, hydroxycarbonyl, alkylcarbonyl, alkoxy-carbonyl, trifluoromethyl, halogen, cyano, hydroxy or nitro, and the salts thereof, the solvates thereof and the solvates of the salts thereof.

Compounds of the invention are the compounds of the formula (I) and the salts, solvates and solvates of the salts thereof, compounds mentioned hereinafter as exemplary embodiment(s) and the salts, solvates and solvates of the salts thereof, where the compounds which are encompassed by formula (I) and are mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds of the invention can exist in tautomeric forms, the present invention includes all tautomeric forms.

Salts preferred for the purposes of the present invention are physiologically acceptable salts of the compounds of the invention. However, salts which are not themselves suitable for pharmaceutical applications but can be used for example for isolating or purifying the compounds of the invention are also included.

Physiologically acceptable salts of the compounds of the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluene-sulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds of the invention which form a complex in the solid or liquid state by coordination with solvent molecules. Hydrates are a special form of solvates in which the coordination takes place with water.

For the purposes of the present invention, unless specified otherwise, the substituents have the following meaning:

Alkyl per se and "alk" and "alkyl" in alkoxy, alkylthio, alkylamino, alkylcarbonyl, alkylsulphonyl, alkylaminosulphonyl and alkoxycarbonyl are a linear or branched alkyl radical having normally 1 to 6, preferably 1 to 4, particularly preferably 1 to 3, carbon atoms, by way of example and preferably methyl, ethyl, n-propyl, isopropyl, tert-butyl, n-pentyl and n-hexyl.

Alkoxy is, by way of example and preferably, methoxy, ethoxy, n-propoxy, isopropoxy, tert-butoxy, n-pentoxy and n-hexoxy.

Alkylthio is, by way of example and preferably, methylthio, ethylthio, n-propylthio, isopropylthio, tert-butylthio, n-pentylthio and n-hexylthio.

Alkylamino is an alkylamino radical having one or two alkyl substituents (chosen independently of one another) by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propyl-amino, N-tert-butyl-N-methylamino, N-ethyl-N-n-pentylamino and N-n-hexyl-N-methylamino. $C_1$-$C_3$-alkylamino is for example a monoalkylamino radical having 1 to 3 carbon atoms or a dialkylamino radical having in each case 1 to 3 carbon atoms per alkyl substituent.

Alkylsulphonyl is, by way of example and preferably, methylsulphonyl, ethylsulphonyl, n-propyl-sulphonyl, isopropylsulphonyl, tert-butylsulphonyl, n-pentylsulphonyl and n-hexylsulphonyl.

Alkylaminosulphonyl is an alkylaminosulphonyl radical having one or two alkyl substitutents (chosen independently of one another), by way of example and preferably, methylaminosulphonyl, ethylaminosulphonyl, n-propylaminosulphonyl, isopropylaminosulphonyl, tert-butylaminosulphonyl, n-pentylaminosulphonyl, n-hexyl-aminosulphonyl, N,N-dimethylaminosulphonyl, N,N-diethyl-aminosulphonyl, N-ethyl-N-methylaminosulphonyl, N-methyl-N-n-propylaminosulphonyl, N-isopropyl-N-n-propylaminosulphonyl, N-tert-butyl-N-methylaminosulphonyl, N-ethyl-N-n-pentylaminosulphonyl and N-n-hexyl-N-methylaminosulphonyl. $C_1$-$C_3$-Alkylaminosulphonyl is for example a monoalkyl-aminosulphonyl radical having 1 to 3 carbon atoms or a dialkylaminosulphonyl radical having in each case 1 to 3 carbon atoms per alkyl substituent.

Alkylcarbonyl is, by way of example and preferably, acetyl and propanoyl.

Alkoxycarbonyl is, by way of example and preferably, methoxycarbonyl, ethoxycarbonyl, n-propoxycarbonyl, isopropoxycarbonyl, tert-butoxycarbonyl, n-pentoxycarbonyl and n-hexoxycarbonyl.

Aryl is a mono- to tricyclic aromatic carbocyclic radical having normally 6 to 14 carbon atoms, by way of example and preferably phenyl, naphthyl and phenanthrenyl.

Halogen is fluorine, chlorine, bromine and iodine, preferably fluorine and chlorine.

A symbol * on a carbon atom means that, in relation to the configuration at this carbon atom, the compound is in enantiopure form, by which is meant for the purposes of the present invention an enantiomeric excess of more than 90% (>90% ee).

Preference is given to those compounds of the formula (I) in which

Ar is phenyl, in which phenyl may be substituted by 1 to 3 substituents, where the substituents are selected independently of one another from the group consisting of $C_1$-$C_6$-alkyl, $C_1$-$C_6$-alkoxy, hydroxycarbonyl, $C_1$-$C_6$-alkylcarbonyl, $C_1$-$C_6$-alkoxycarbonyl, trifluoromethyl, fluorine, chlorine, bromine, cyano, hydroxy, amino, $C_1$-$C_6$-alkylamino and nitro, or two of the substituents on the phenyl form together with the carbon atoms to which they are bonded a 1,3-dioxolane, and an optionally present third substituent is selected independently thereof from the said group, $Q^1$, $Q^2$ and $Q^3$ are CH or N, where always exactly one of $Q^1$, $Q^2$ and $Q^3$ is N and the others are simultaneously CH, $Q^4$ is CH, $R^1$ is hydrogen, $C_1$-$C_3$-alkyl, $C_1$-$C_3$-alkoxy, $C_1$-$C_3$-alkylthio, fluorine or chlorine, $R^2$ is hydrogen, $C_1$-$C_3$-alkyl, $C_1$-$C_3$-alkoxy, $C_1$-$C_3$-alkylthio, fluorine or chlorine, $R^3$ is $C_1$-$C_4$-alkyl, cyano, fluorine, chlorine, nitro, trifluoromethyl or $C_1$-$C_3$-alkylsulphonyl, or one of the radicals $R^1$, $R^2$ and $R^3$ is hydrogen, $C_1$-$C_3$-alkyl, $C_1$-$C_3$-alkoxy, cyano, halogen, nitro or trifluoromethyl, and the other two form together with the carbon atoms to which they are bonded a cyclopentane ring or a cyclohexane ring, $R^4$ is hydrogen or methyl, $R^5$ is hydrogen, $R^6$ is hydrogen, $C_1$-$C_3$-alkyl, $C_1$-$C_3$-alkoxy, hydroxycarbonyl, aminocarbonyl, trifluoromethyl, fluorine, chlorine, cyano, hydroxy or nitro, and $R^7$ is hydrogen, $C_1$-$C_3$-alkyl, $C_1$-$C_3$-alkoxy, fluorine, chlorine, cyano or hydroxy.

Preference is given among these in particular to those compounds of the formula (I) in which Ar is phenyl, in which phenyl may be substituted by 1 to 2 substituents, where the substituents are selected independently of one another from the group consisting of methyl, methoxy, fluorine and chlorine, $Q^1$, $Q^2$ and $Q^3$ is CH or N, where always exactly one of $Q^1$, $Q^2$ and $Q^3$ is N, and the others are simultaneously CH, $Q^4$ is CH, $R^1$ is hydrogen, methyl, methoxy, methylthio, fluorine or chlorine, $R^2$ is hydrogen, $R^3$ is methyl, isopropyl, tert-butyl, cyano, fluorine, chlorine, nitro or trifluoromethyl, $R^4$ is hydrogen, $R^5$ is hydrogen, $R^6$ is hydrogen, aminocarbonyl, fluorine, chlorine, cyano or hydroxy, and $R^7$ is hydrogen.

Preference is given among these very particularly to those compounds of the formula (I) in which
Ar is phenyl, in which phenyl may be substituted by 1 to 2 substituents, where the substituents are selected independently of one another from the group consisting of methyl, methoxy, fluorine and chlorine,
$Q^1$, $Q^2$ and $Q^3$ are CH or N,
where always exactly one of $Q^1$, $Q^2$ and $Q^3$ is N, and the others are simultaneously CH,
$Q^4$ is CH,
$R^1$ is hydrogen, methyl or methoxy,
$R^2$ is hydrogen,
$R^3$ is methyl, tert-butyl, chlorine or trifluoromethyl,
$R^4$ is hydrogen,
$R^5$ is hydrogen,
$R^6$ is hydrogen and $R^7$ is hydrogen.

Preference is also given to those compounds of the formula (I) in which $R^1$ is hydrogen, methyl, methoxy or fluorine.

Preference is given among these in particular to those compounds of the formula (I) in which $R^1$ is methoxy.

Preference is also given to those compounds of the formula (I) in which $R^1$ is bonded to the phenyl ring via the position ortho to the point of linkage of the phenyl ring. The point of linkage of the phenyl ring substituted by the radicals $R^1$, $R^2$ and $R^3$ means in the context of the present invention that carbon atom of the phenyl ring which is linked to one of the two dihydroquinazoline nitrogen atoms according to formula (I).

Particular preference is given to those compounds of the formula (I) in which $R^1$ is methoxy, and $R^1$ is bonded to the phenyl ring via the position ortho to the point of linkage of the phenyl ring.

Preference is also given to those compounds of the formula (I) in which $R^2$ is hydrogen.

Preference is also given to those compounds of the formula (I) in which $R^3$ is trifluoromethyl, chlorine, methyl, isopropyl or tert-butyl.

Preference is given among these in particular to those compounds of the formula (I) in which $R^3$ is trifluoromethyl, chlorine or methyl.

Preference is given among these very particularly to those compounds of the formula (I) in which $R^3$ is trifluoromethyl.

Preference is also given to those compounds of the formula (I) in which $R^1$ is bonded to the phenyl ring via the position ortho to the point of linkage of the phenyl ring, and $R^3$ is bonded to the phenyl ring via the position opposite to $R^1$ and meta to the point of linkage of the phenyl ring.

Particular preference is given to those compounds of the formula (I) in which $R^1$ is bonded to the phenyl ring via the position ortho to the point of linkage of the phenyl ring, $R^3$ is trifluoromethyl, chlorine or methyl, and $R^3$ is bonded to the phenyl ring via the position opposite to $R^1$ and meta to the point of linkage of the phenyl ring.

Particular preference is given among these to those compounds of the formula (I) in which $R^1$ is bonded to the phenyl ring via the position ortho to the point of linkage of the phenyl ring, $R^3$ is trifluoromethyl, and $R^3$ is bonded to the phenyl ring via the position opposite to $R^1$ and meta to the point of linkage of the phenyl ring.

Preference is also given to those compounds of the formula (I) in which $R^4$ and $R^5$ are hydrogen.

Preference is also given to those compounds of the formula (I) in which $R^6$ is hydrogen.

Preference is also given to those compounds of the formula (I) in which $R^7$ is hydrogen.

Preference is also given to those compounds of the formula (I) in which Ar is phenyl, in which phenyl may be substituted by 1 to 2 substituents, where the substituents are selected independently of one another from the group consisting of methyl, methoxy and fluorine and chlorine.

The definitions of radicals indicated specifically in the respective combinations or preferred combinations of radicals are replaced irrespective of the particular combinations indicated for the radicals as desired also by definitions of radicals of another combination.

Combinations of two or more of the abovementioned preferred ranges are very particularly preferred.

The invention further relates to a process for preparing compounds of the formula (I), where compounds of the formula

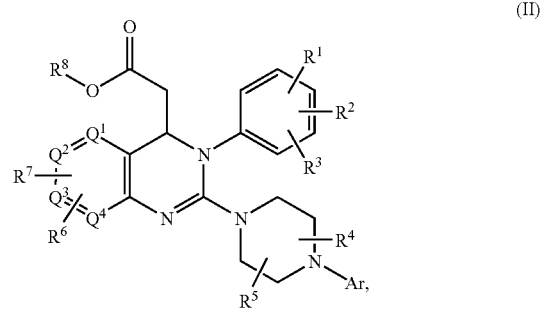

(II)

in which

Ar, $Q^1$, $Q^2$, $Q^3$, $Q^4$, $R^1$, $R^2$, $R^3$, $R^4$, $R^5$, $R^6$ and $R^7$ have the meaning indicated above, and $R^8$ is alkyl, preferably methyl or ethyl, or tert-butyl, are reacted with bases or acids.

The reaction in the case of methyl and ethyl generally takes place with bases in inert solvents, preferably in a temperature range from room temperature to reflux of the solvents under atmospheric pressure.

Examples of bases are alkali metal hydroxides such as sodium, lithium or potassium hydroxide, or alkali metal carbonates such as caesium carbonate, sodium or potassium carbonate, where appropriate in aqueous solution, with preference for sodium hydroxide in water.

Examples of inert solvents are ethers such as 1,2-dimethoxyethane, dioxane, tetrahydrofuran, glycol dimethyl ether or diethylene glycol dimethyl ether, alcohols such as methanol, ethanol, n-propanol, isopropanol, n-butanol or tert-butanol, or mixtures of solvents, with preference for dioxane or tetrahydrofuran.

In the case of tert-butyl, the reaction generally takes place with acids in inert solvents, preferably in a temperature range from 0° C. to 40° C. under atmospheric pressure.

Acids suitable in this connection are hydrogen chloride in dioxane, hydrogen bromide in acetic acid or trifluoroacetic acid in methylene chloride.

The compounds of the formula (II) are known or can be prepared by reacting compounds of the formula

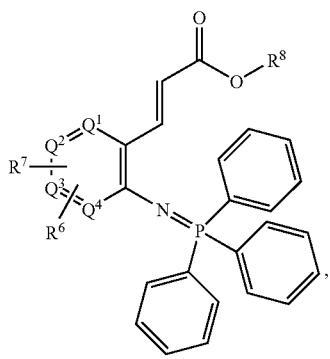

(III)

in which $Q^1$, $Q^2$, $Q^3$, $Q^4$, $R^6$, $R^7$ and $R^8$ have the meaning indicated above, in a two-stage reaction firstly with compounds of the formula

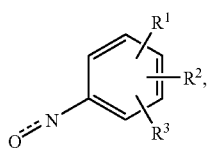

(IV)

in which $R^1$, $R^2$ and $R^3$ have the meaning indicated above, and subsequently with compounds of the formula

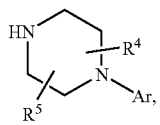

(V)

in which

Ar, $R^4$ and $R^5$ have the meaning indicated above.

The reaction takes place in both stages generally in inert solvents, preferably in a temperature range from room temperature to 100° C. under atmospheric pressure. Silica gel is added where appropriate to the reaction mixture in the second stage. The reaction preferably takes place with a working up between the first and second stage.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, 1,2-dimethoxyethane, dioxane, tetrahydrofuran, glycol dimethyl ether or diethylene glycol dimethyl ether, hydrocarbons such as benzene, xylene, toluene, hexane, cyclohexane or petroleum fractions, or other solvents such as dimethylformamide, dimethylacetamide, acetonitrile or ethyl acetate, or mixtures of solvents, with preference for methylene chloride.

The compounds of the formula (IV) are known or can be synthesized by known processes from appropriate precursors.

The compounds of the formula (V) are known or can be synthesized by known processes from appropriate precursors, for example by a Buchwald-Hartwig reaction in accordance with the following synthesis scheme (review in: C. G. Frost, P. Mendonca, *J. Chem. Soc., Perkin Trans I*, 1998, 2615-2623):

Buchwald-Hartwig reaction:

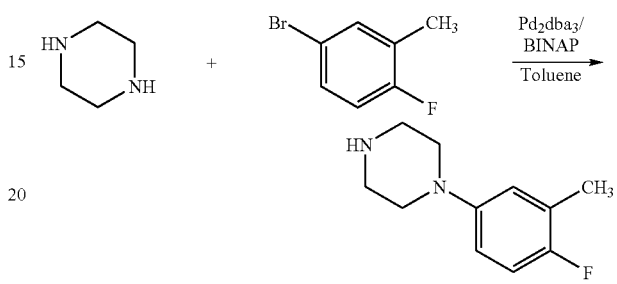

The precursors required for this are known or can be synthesized by known processes from appropriate precursors.

The compounds of the formula (III) are known or can be prepared by reacting compounds of the formula

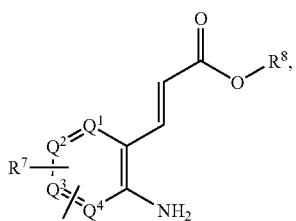

(VI)

in which $Q^1$, $Q^2$, $Q^3$, $Q^4$, $R^6$, $R^7$ and $R^8$ have the meaning indicated above, with triphenylphosphine and tetrachloromethane.

The reaction generally takes place in inert solvents in the presence of a base, preferably in a temperature range from room temperature to 50° C. under atmospheric pressure.

Examples of inert solvents are ethers such as diethyl ether, methyl tert-butyl ether, 1,2-dimethoxyethane, dioxane, tetrahydrofuran, glycol dimethyl ether or diethylene glycol dimethyl ether, hydrocarbons such as benzene, xylene, toluene, hexane, cyclohexane or petroleum fractions, or other solvents such as dimethylformamide, dimethylacetamide, acetonitrile or pyridine, with preference for acetonitrile.

Examples of bases are alkali metal and alkaline earth metal carbonates such as caesium carbonate, sodium or potassium carbonate or amines such as triethylamine, diisopropylethylamine, N-methyl-morpholine or pyridine, with preference for triethylamine.

The compounds of the formula (VI) are known or can be synthesized by known processes from appropriate precursors, for example by a Heck reaction or a Wittig-Horner reaction according to the following synthesis schemes:

Heck Reaction:

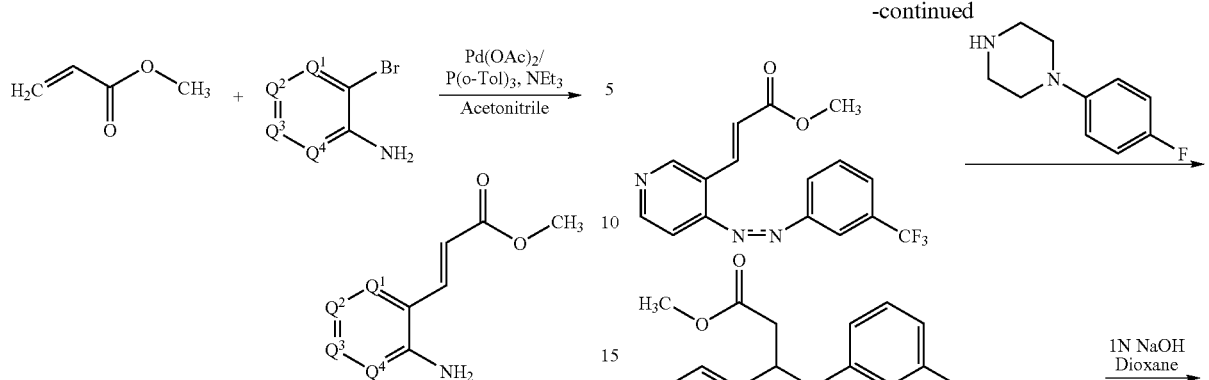

Wittig-Horner Reaction:

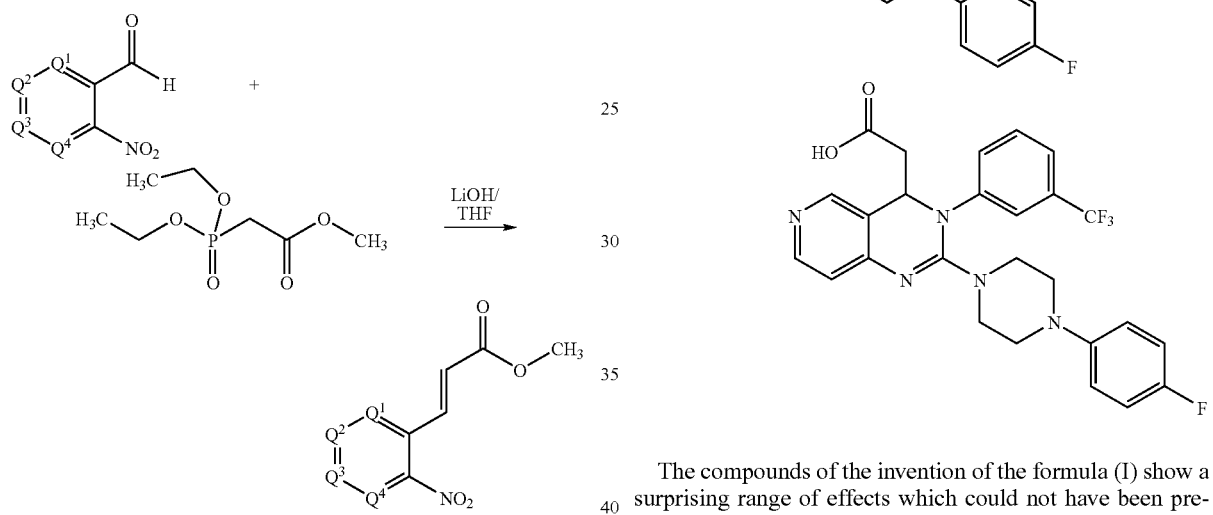

The precursors required for this are known or can be synthesized by known processes from appropriate precursors.

Preparation of the compounds of the invention can be illustrated by the following synthesis scheme.

Synthesis Scheme:

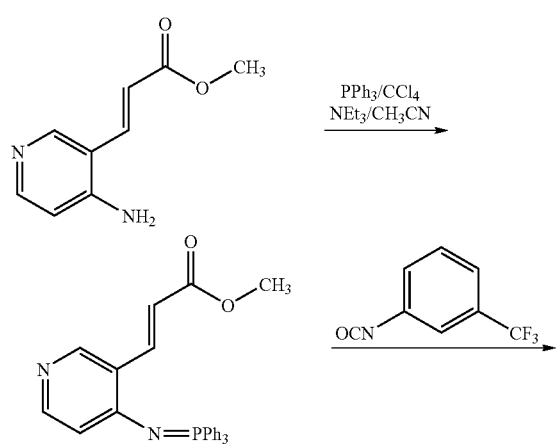

The compounds of the invention of the formula (I) show a surprising range of effects which could not have been predicted. They show an antiviral effect on representatives of the group of Herpes viridae (herpes viruses), in particular on cytomegaloviruses (CMV) especially on human cytomegalovirus (HCMV).

Areas of indication which may be mentioned by way of example are:

1) Treatment and prophylaxis of HCMV infections in AIDS patients (retinitis, pneumonitis, gastrointestinal infections).
2) Treatment and prophylaxis of cytomegalovirus infections in bone-marrow and organ transplant patients who develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of HCMV infection in immunosuppressed patients associated with cancer and cancer therapy.
6) Treatment of HCMV-positive cancer patients with the aim of reducing HCMV-mediated tumour progression (cf. J. Cinati, et al., *FEMS Microbiology Reviews* 2004, 28, 59-77).

The present invention further relates to the use of the compounds of the invention for the treatment and/or prophylaxis of diseases, in particular of infections with viruses, especially the aforementioned viruses, and of the infectious diseases caused thereby. A viral infection means hereinafter both an infection with a virus and a disease caused by an infection with a virus.

The invention further relates to the use of the compounds of the invention for the treatment and/or prophylaxis of disorders, especially of the aforementioned disorders.

The present invention further relates to the use of the compounds of the invention for producing a medicament for the treatment and/or prophylaxis of disorders, especially the aforementioned disorders.

The compounds of the invention are preferably used to produce medicaments which are suitable for the prophylaxis and/or treatment of infections with a representative of the group of Herpes viridae, particularly a cytomegalovirus, in particular human cytomegalovirus.

The present invention further relates to a method for the treatment and/or prophylaxis of disorders, especially the aforementioned disorders, by using an antivirally effective amount of the compounds of the invention.

The present invention further relates to medicaments comprising at least one compound of the invention and at least one or more further active ingredients, in particular for the treatment and/or prophylaxis of the aforementioned disorders. Suitable active ingredients in the combination which may be mentioned by way of example and preferably are: antiviral active ingredients such as gancyclovir or acyclovir.

The compounds of the invention may have systemic and/or local effects. They can for this purpose be administered in a suitable way, such as, for example, by the oral, parenteral, pulmonary, nasal, sublingual, lingual, buccal, rectal, dermal, transdermal, conjunctival, otic or topical route, or as implant or stent.

For these administration routes it is possible to administer the compounds of the invention in suitable administration forms.

Suitable for oral administration are administration forms which function according to the prior art and deliver the compounds of the invention rapidly and/or in modified manner and which comprise the compounds of the invention in crystalline and/or amorphicized and/or dissolved form, such as, for example, tablets (uncoated or coated tablets, for example with coatings which are resistant to gastric juice or dissolve with a delay or are insoluble and control the release of the compound of the invention), tablets which disintegrate rapidly in the oral cavity, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of absorption (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilisates or sterile powders.

Examples suitable for the other administration routes are pharmaceutical forms for inhalation (inter alia powder inhalers, nebulizers), nasal drops, solutions, sprays; tablets, films/wafers or capsules, to be administered lingually, sublingually or buccally, suppositories, preparations for the eyes and ears, vaginal capsules, aqueous suspensions (lotions, shaking mixtures), lipophilic suspensions, ointments, creams, transdermal therapeutic systems, milk, pastes, foams, dusting powders, implants or stents.

The compounds of the invention can be converted into the stated administration forms. This can take place in a manner known per se by mixing with inert, non-toxic, pharmaceutically suitable excipients. These include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants such as ascorbic acid), colours (for example inorganic pigments such as iron oxides) or flavour- and/or odour-masking agents.

The present invention further relates to medicaments which comprise at least one compound of the invention, usually together with one or more inert, non-toxic, pharmaceutically suitable excipients, and to the use thereof for the aforementioned purposes.

It has generally proved advantageous to administer on intravenous administration amounts of about 0.001 to 10 mg/kg, preferably about 0.01 to 5 mg/kg, of body weight to achieve effective results, and the dosage on oral administration is about 0.01 to 25 mg/kg, preferably 0.1 to 10 mg/kg, of body weight.

It may nevertheless be necessary where appropriate to deviate from the amounts mentioned, specifically as a function of the body weight, administration route, individual response to the active ingredient, mode of preparation and time or interval over which administration takes place. Thus, it may be sufficient in some cases to make do with less than the aforementioned minimum amount, whereas in other cases the upper limit mentioned must be exceeded. It may in the event of administration of larger amounts be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

| Abbreviations: | |
|---|---|
| BINAP | 2,2'-Bis(diphenylphosphino)-1,1'-binaphthyl |
| ca. | circa |
| $CDCl_3$ | deuterochloroform |
| conc. | concentrated |
| DCI | direct chemical ionization (in MS) |
| DCM | dichloromethane |
| DIEA | N,N-diisopropylethylamine |
| DMSO | dimethylsulphoxide |
| DMF | N,N-dimethylformamide |
| EE | ethyl acetate (acetic acid ethyl ester) |
| EI | electron impact ionization (in MS) |
| ESI | electrospray ionization (in MS) |
| h | hour |
| HPLC | high pressure, high performance liquid chromatography |
| LC-MS | coupled liquid chromatography-mass spectroscopy |
| LDA | lithium diisopropylamide |
| Min | minutes |
| m.p. | melting point |
| MS | mass spectroscopy |
| MTBE | Methyl tert-butyl ether |
| NMR | nuclear magnetic resonance spectroscopy |
| Pd-C | palladium on carbon |
| RP-HPLC | reverse phase HPLC |
| RT | room temperature |
| $R_t$ | retention time (in HPLC) |
| sat. | saturated |
| THF | tetrahydrofuran |
| TLC | thin layer chromatography |

General LC-MS and HPLC Methods:

Method 1 (analytical HPLC): Instrument: HP 1100 with DAD detection; column: Kromasil RP-18, 60 mm×2 mm, 3.5

μm; eluent A: 5 ml HClO4/l water, eluent B: acetonitrile; gradient: 0 min 2% B, 0.5 min 2% B, 4.5 min 90% B, 6.5 min 90% B; flow rate: 0.75 ml/min; oven: 30° C.; UV detection: 210 nm.

Method 2 (preparative HPLC, laboratory HPLC): Column: CromSil C18, 250 mm×30 mm; flow rate: 50 ml/min; running time: 38 min; eluent A: water, eluent B: acetonitrile, gradient 10% B (3 min)→90% B (31 min)→90% B (34 min)→10% B (34.01 min): UV detection: 210 nm.

Method 3 (LCMS): Instrument: Micromass Quattro LCZ, with HPLC Agilent series 1100; column: Grom-SIL120 ODS-4 HE, 50 mm×2.0 mm, 3 μm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Starting Compounds

Example 1A

Pyridin-4-yl tert-butyl carbamate

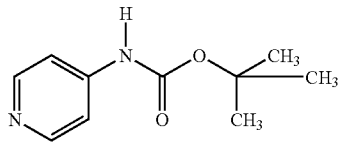

2.0 g (21.3 mmol) of 4-aminopyridine are added in portions to a solution of 5.1 g (23.4 mmol) of di-tert-butyl dicarbonate in 20 ml of THF. After the addition is complete, the mixture is stirred at room temperature for 1 h, then the solvent is removed in vacuo, and the residue obtained in this way is suspended in diethyl ether. The solid is filtered off and dried in vacuo. Yield: 3.43 g (83% of theory).

HPLC (method 1): $R_t$=3.42 min
MS (ESI-pos): m/z=195 [M+H]$^+$

Example 2A

Pyridin-3-yl tert-butyl carbamate

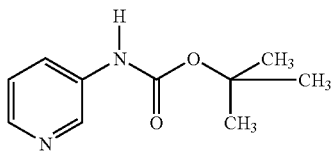

18.2 g (40.9 mmol) of lead(IV) acetate are added to a solution of 5.0 g (40.9 mmol) of nicotinamide in 100 ml of tert-butanol, and the reaction mixture is stirred under reflux for 4 h. The mixture is then filtered through kieselguhr, the solvent is removed in vacuo, and the residue is taken up in diethyl ether. The organic phase is washed with saturated sodium bicarbonate solution and saturated sodium chloride solution, dried over sodium sulphate and filtered. The solution is mixed with pentane, and the resulting precipitate is filtered off and dried. Yield: 2.79 g (35% of theory).

HPLC (Method 1): $R_t$=3.36 min
MS (ESI-pos): m/z=195 [M+H]$^+$

Example 3A (3-Formylpyridin-4-yl) tert-butyl carbamate

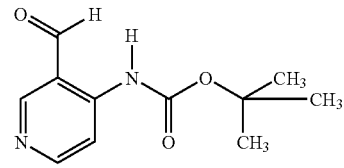

4.12 g (21.3 mmol) of the Boc-protected aminopyridine from Example 1A are dissolved in 75 ml of tetrahydrofuran, the solution is cooled to −78° C. under argon, and 34 ml of a 1.5M solution (51.1 mmol) of tert-butyllithium in pentane are added dropwise. The addition takes place so that the internal temperature remains below −65° C. After the addition is complete, the mixture is stirred at −20° C. for 1 h. Then 10.6 ml (138.3 mmol) of absolute N,N-dimethylformamide are added to the mixture so that the reaction temperature remains below −15° C. during the addition. The reaction is stirred at room temperature for 16 h and then, while cooling in ice, 1N hydrochloric acid is added. The pH is adjusted to pH 7 with solid sodium carbonate, ethyl acetate is added to the mixture, and the organic phase is washed with water and saturated sodium chloride solution. The organic phase is separated off and dried over sodium sulphate, and the solvent is removed in vacuo. The product is purified by chromatography on silica gel with cyclohexane/ethyl acetate (3:2 v/v). 3.15 g (63% of theory) of product are obtained.

HPLC (method 1): $R_t$=3.65 min
MS (ESI-pos): m/z=223 [M+H]$^+$

Example 4A (4-Formylpyridin-3-yl) tert-butyl carbamate

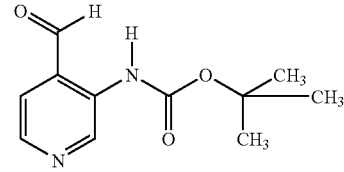

2.7 g (13.9 mmol) of the Boc-protected aminopyridine from Example 2A are dissolved in 50 ml of tetrahydrofuran, the solution is cooled to −78° C. under argon, and 22.4 ml of a 1.5 M solution (33.4 mmol) of tert-butyllithium in pentane are added dropwise. The addition takes place so that the internal temperature remains below −65° C. After the addition is complete, the mixture is stirred at −20° C. for 1 h. Then 4.6 ml (41.7 mmol) of N-formylpiperidine are added to the mixture so that the reaction temperature remains below −15° C. during the addition. The reaction is stirred at room temperature for 16 h and then, while cooling in ice, 1N hydrochloric acid is added. The pH is adjusted to pH 7 with solid sodium carbonate, ethyl acetate is added to the mixture, and the organic phase is washed with water and saturated sodium chloride solution. The organic phase is separated off and dried over sodium sulphate, and the solvent is removed in vacuo. The product is purified by chromatography on silica gel with cyclohexane/ethyl acetate (7:3 v/v). 1.54 g (49% of theory) of product are obtained.

HPLC (method 1): $R_t$=3.40 min
MS (ESI-pos): m/z=223 [M+H]$^+$

Example 5A

3-Amino-2-bromopyridine

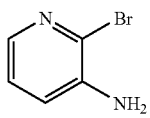

4.00 g (42.5 mmol) of 3-aminopyridine are dissolved in 200 ml of acetonitrile and, after addition of 8.32 g (46.8 mmol) of N-bromosuccinimide, stirred at room temperature with exclusion of light for 20 h. The reaction mixture is then concentrated, suspended in ethyl acetate and washed with saturated aqueous sodium bicarbonate solution and saturated aqueous sodium chloride solution. The organic phase is dried over sodium sulphate, filtered and concentrated. Purification is by column chromatography on silica gel with cyclohexane/ethyl acetate (1:1). 969 mg (12% of theory) of product are obtained.
HPLC (method 1): $R_t$=1.08 min.
MS (ESI-pos): m/z=173 [M+H]$^+$

Example 6A tert-Butyl (2E)-3-(3-aminopyridin-2-yl)acrylate

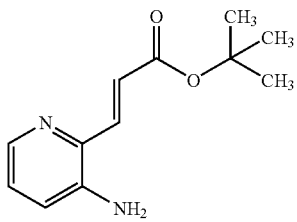

950 mg (4.94 mmol) of the bromide from Example 5A, 1900 mg (14.83 mmol) of tert-butyl acrylate, 330 mg (1.50 mmol) of palladium(II) acetate, 450 mg (1.50 mmol) of tri-ortho-tolylphospine are dissolved in 15 ml of acetonitrile, and 1000 mg (9.88 mmol) of triethylamine are added. The mixture is stirred under reflux for 16 h. The reaction mixture is concentrated, mixed with ethyl acetate and washed with saturated aqueous sodium chloride solution. The organic phase is dried over sodium sulphate, filtered, concentrated and purified by column chromatography on silica gel with cyclohexane/ethyl acetate (7:3). 95 mg (6% of theory) of product are obtained.

Example 7A

Methyl (2E)-3-{4-[(tert-butoxycarbonyl)amino]pyridin-3-yl}acrylate

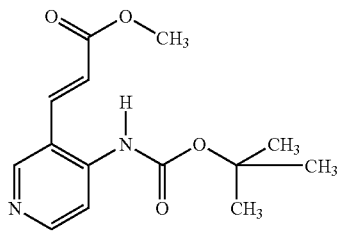

A suspension of 3.0 g (13.5 mmol) of the aldehyde from Example 3A, 3.12 g (14.8 mmol) of methyl diethyl phosphonoacetate and 623 mg (14.8 mmol) of lithiumhydroxidemonohydrate in 30 ml of tetrahydrofuran is stirred at room temperature for 16 h. This is followed by addition of 30 ml of water and extraction with ethyl acetate. The organic phase is separated off, washed with saturated sodium chloride solution, dried over sodium sulphate and filtered, and the solvent is removed in vacuo. The residue is dried at 100° C./1 mbar. 3.5 g (89% of theory) of the title compound were obtained.
HPLC (method 1): $R_t$=3.71 min
MS (ESI-pos): m/z=279 [M+H]$^+$

Example 8A

Methyl (2E)-3-{3-[(tert-butoxycarbonyl)amino]pyridin-4-yl}acrylate

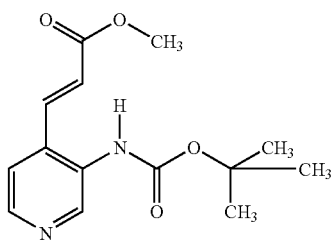

A suspension of 1.48 g (6.66 mmol) of the aldehyde from Example 4A, 1.54 g (7.33 mmol) of methyl diethyl phosphonoacetate and 307 mg (7.33 mmol) of lithiumhydroxidemonohydrate in 15 ml of tetrahydrofuran is stirred at room temperature for 16 h. This is followed by addition of 15 ml of water and extraction with ethyl acetate. The organic phase is separated off, washed with saturated sodium chloride solution, dried over sodium sulphate and filtered, and the solvent is removed in vacuo. The residue is dried at 75° C./1 mbar. 1.82 g (98% of theory) of the title compound are obtained.
HPLC (method 1): $R_t$=3.73 min
MS (ESI-pos): m/z=279 [M+H]$^+$

Example 9A

Methyl (2E)-3-{4-aminopyridin-3-yl}acrylate

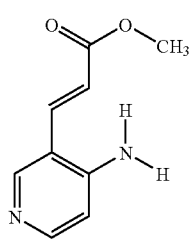

900 mg (3.23 mmol) of the Boc-protected aminopyridine from Example 7A are dissolved in 3 ml of trifluoroacetic acid at 0° C. The reaction mixture is then stirred at room temperature for 1 h, the mixture is introduced into ice-cold sodium bicarbonate solution and stirred for 30 min, and the resulting precipitate is filtered off, washed with water and dried. 242 mg (42% of theory) of the title compound are obtained.
A further 105 mg (18% of theory) of product can be isolated as an oil from the mother liquor by adjusting the pH to pH 10 and extraction with ethyl acetate. The two fractions presumably differ in their degree of protonation.

HPLC (method 1): $R_t$=2.67 min
MS (CI-pos): m/z=179 [M+H]$^+$

Example 10A

Methyl (2E)-3-{3-aminopyridin-4-yl}acrylate

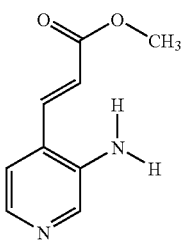

1.8 g (6.47 mmol) of the Boc-protected aminopyridine from Example 8A are dissolved in 18 ml of methanol at room temperature, and 1 ml of concentrated hydrochloric acid is added to the solution. The reaction mixture is then stirred at 70° C. for 4 h, the mixture is introduced into 50 ml of sodium bicarbonate solution, the pH is adjusted to pH 14 by adding 20% strength sodium hydroxide solution, and the mixture is extracted with ethyl acetate. The organic phase is washed with concentrated sodium chloride solution and dried over sodium sulphate, and the solvent is removed in vacuo. Yield: 935 mg (79% of theory).

HPLC (method 1): $R_t$=2.88 min
MS (ESI-pos): m/z=179 [M+H]$^+$

General Procedure [A]: Preparation of Iminophosphoranes from Aminopyridines 1.0 eq. of aminopyridine, 2.0 eq. of triphenylphosphine, 10.0 eq. of tetrachloromethane and 10.0 eq. of triethylamine are suspended in acetonitrile (ca. 0.33 M based on the aminopyridine). The reaction mixture is stirred at room temperature for 16 h, and the solvent is removed in vacuo. The crude product is reacted without further purification or is purified by column chromatography on silica gel.

Example 11A tert-Butyl (2E)-3-{3-[(triphenylphosphoranylidene)amino]pyridin-2-yl}acrylate

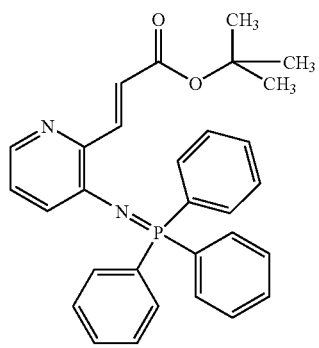

Starting from 95 mg (0.28 mmol) of aminopyridine from Example 6A, general procedure [A] results in the crude product which is purified by column chromatography on silica gel with cyclohexane/ethyl acetate (7:3). 70 mg (51% of theory) of product are obtained.

HPLC (method 1): $R_t$=4.83 min.
MS (ESI-pos): m/z=481 [M+H]$^+$

Example 12A

Methyl (2E)-3-{4-[(triphenylphosphoranylidene)amino]pyridin-3-yl}acrylate

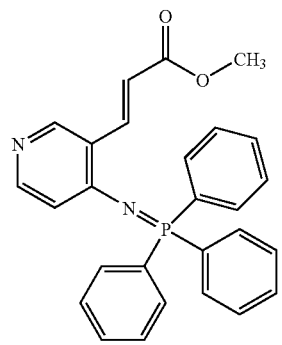

Starting from 320 mg (1.8 mmol) of aminopyridine from Example 9A, general procedure [A] results in 1650 mg of crude product which is reacted without further purification.

Example 13A

Methyl (2E)-3-{3-[(triphenylphosphoranylidene)amino]pyridin-4-yl}acrylate

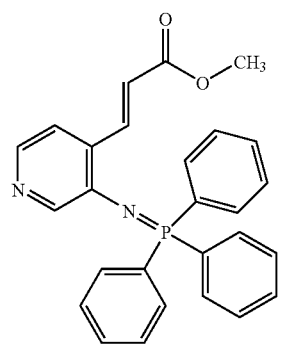

Starting from 900 mg (4.89 mmol) of aminopyridine from Example 10A, general procedure [A] results in 1910 mg of crude product which is reacted without further purification.

MS (ESI-pos): m/z=439 [M+H]$^+$

General Procedure [B]: Preparation of Carbodiimides from Iminophosphoranes by Reaction with Isocyanates 1.0 eq. of iminophosphorane (where appropriate as crude product) is dissolved in dichloromethane, 1.1 eq. of isocyanate are added, and the reaction mixture is stirred at room temperature for 16 h. The crude product obtained in this way is directly reacted further.

Example 14A tert-Butyl (2E)-3-{3-[({[3-(trifluoromethyl)phenyl]imino}methylene)amino]pyridin-2-yl}acrylate

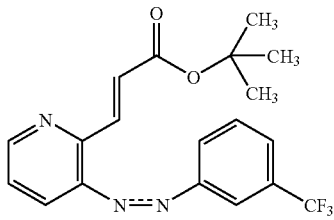

65 mg (0.14 mmol) of iminophosphorane from Example 11A are reacted by general procedure [B] with 27 mg (0.14 mmol) of 3-trifluoromethylphenyl isocyanate, and the crude product is reacted further without purification.

Example 15A

Methyl (2E)-3-{4-[({[3-(trifluoromethyl)phenyl]imino}methylene)amino]pyridin-3-yl}acrylate

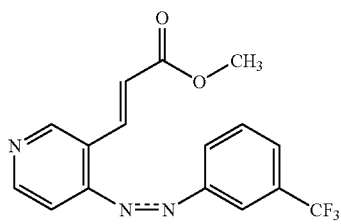

300 mg (0.34 mmol) of iminophosphorane from Example 12A are reacted by general procedure [B] with 70 mg (0.38 mmol) of 3-trifluoromethylphenyl isocyanate, and the crude product is reacted further without purification.

Example 16A

Methyl (2E)-3-[4-({[(2-methoxy-5-methylphenyl)imino]methylene}amino)pyridin-3-yl]acrylate

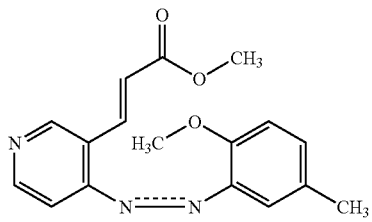

150 mg (0.28 mmol) of iminophosphorane from Example 12A are reacted by general procedure [B] with 67 mg (0.42 mmol) of 1-methoxy-4-methylphenyl isocyanate, and the crude product is reacted further without purification.

Example 17A

Methyl (2E)-3-{3-[({[3-(trifluoromethyl)phenyl]imino}methylene)amino]pyridin-4-yl}acrylate

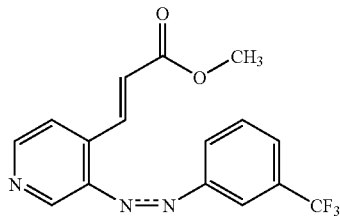

1000 mg (1.37 mmol) of aminopyridine from Example 13A are reacted by general procedure [B] with 282 mg (1.51 mmol) of 3-trifluoromethylphenyl isocyanate, and the crude product is reacted further without purification.

Example 18A

Methyl (2E)-3-{4-[({[2-methoxy-5-(trifluoromethyl)phenyl]imino}methylene)amino]pyridin-3-yl}acrylate

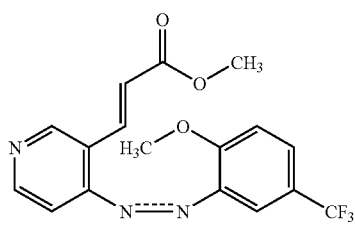

1017 mg (1.90 mmol) of iminophosphorane from Example 12A are reacted by general procedure [B] with 413 mg (1.90 mmol) of 1-methoxy-4-trifluoromethylphenyl isocyanate, and the crude product is reacted further without purification.

Example 19A

2-Isocyanato-1-methoxy-4-(trifluoromethyl)benzene

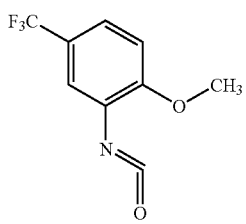

3 g (15.69 mmol) of 2-methoxy-5-trifluoromethylaniline are dissolved in 100 ml of dichloromethane, and 6.73 g (31.39 mmol) of 1,8-bis(dimethylamino)naphthalene are added. At 0-5° C., 2.24 g (11.3 mmol) of trichloromethyl chloroformate, dissolved in 50 ml of dichloromethane, are added dropwise, and the mixture is stirred at 0° C. for 30 min and at room temperature for 60 min. It is washed at 0° C. with 1N hydrochloric acid, ice-water and sodium bicarbonate solution. The product is obtained after drying over magnesium sulphate and removal of the solvent by distillation. The isocyanate is then reacted without further purification in the following reactions. Yield: 3 g (88% of theory)

General Procedure [C]: Reaction of Carbodiimides with Phenylpiperazines to Give Dihydropyridopyrimidinylacetic Esters 1.0 eq of carbodiimide (where appropriate as crude product) is dissolved in dichloromethane, 1.05 eq of phenylpiperazine and a spatula tip of silica gel are added, and the reaction mixture is stirred under reflux for 16 h. The solvent is then removed in vacuo, and the product is purified by chromatography on silica gel or by preparative HPLC (method 2).

Example 20A

Methyl {2-[4-(4-fluorophenyl)piperazin-1-yl]-3-[3-(trifluoromethyl)phenyl]-3,4-dihydropyrido-[3,4-d]pyrimidin-4-yl}acetate

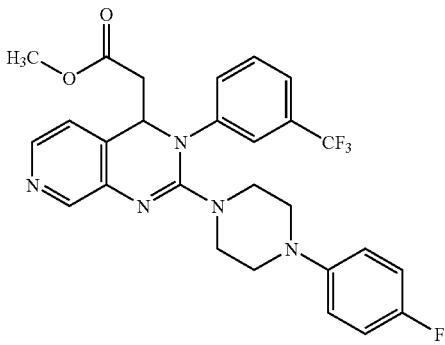

Starting from 250 mg (0.34 mmol) of the carbodiimide from 17 A and 65 mg (0.36 mmol) of 4-fluorophenylpiperazine, general procedure [C] and purification twice by preparative HPLC result in 64 mg (33% of theory) of product.
HPLC (method 1): $R_t$=4.42 min
MS (ESI-pos): m/z=528 [M+H]$^+$ Example 21A Methyl {2-[4-(3-methylphenyl)piperazin-1-yl]-3-[3-(trifluoromethyl)phenyl]-3,4-dihydropyrido-[3,4-d]pyrimidin-4-yl}acetate

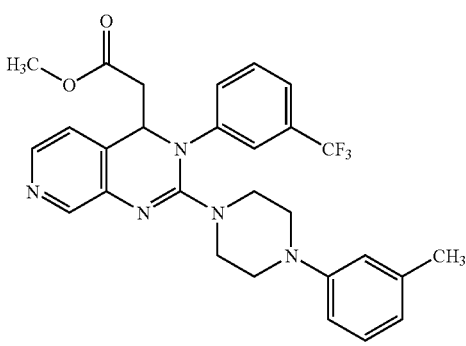

Starting from 250 mg (0.34 mmol) of the carbodiimide from Example 17A and 63 mg (0.36 mmol) of 3-methylphenylpiperazine, general procedure [C] and purification by preparative HPLC result in 88 mg (48% of theory) of product.
HPLC (method 1): $R_t$=4.42 min
MS (ESI-pos): m/z=524 [M+H]$^+$ Example 22A Methyl {2-[4-(3-chlorophenyl)piperazin-1-yl]-3-[3-(trifluoromethyl)phenyl]-3,4-dihydropyrido-[3,4-d]pyrimidin-4-yl}acetate

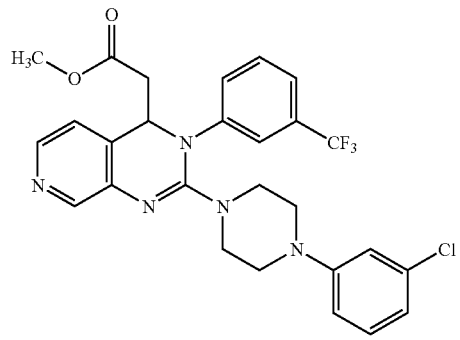

Starting from 250 mg (0.34 mmol) of the carbodiimide from Example 17A and 71 mg (0.36 mmol) of 3-chlorophenylpiperazine, general procedure [C] and purification by preparative HPLC result in 102 mg (53% of theory) of product.
HPLC (method 1): $R_t$=4.65 min
MS (ESI-pos): m/z=544 [M+H]$^+$ Example 23A Methyl {2-[4-(3-methoxyphenyl)piperazin-1-yl]-3-[3-(trifluoromethyl)phenyl]-3,4-dihydropyrido-[3,4-d]pyrimidin-4-yl}acetate

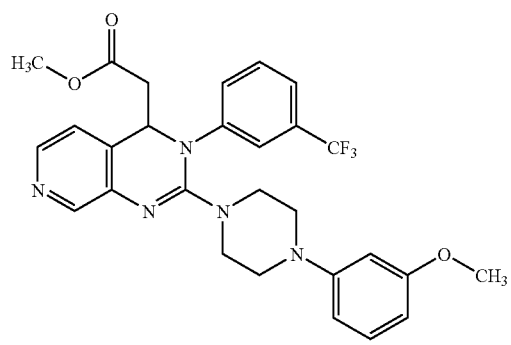

Starting from 250 mg (0.34 mmol) of the carbodiimide from Example 17A and 69 mg (0.36 mmol) of 3-methoxyphenylpiperazine, general procedure [C] and purification by preparative HPLC result in 90 mg (46% of theory) of product.
HPLC (method 1): $R_t$=4.40 min
MS (ESI-pos): m/z=540 [M+H]$^+$

Example 24A

Methyl {2-[4-(4-fluorophenyl)piperazin-1-yl]-3-[3-(trifluoromethyl)phenyl]-3,4-dihydropyrido-[4,3-d]pyrimidin-4-yl}acetate

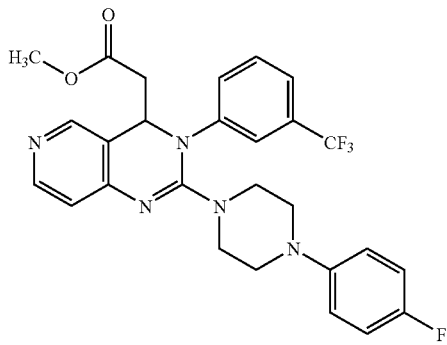

Starting from 107 mg (0.31 mmol) of the carbodiimide from Example 15A and 56 mg (0.31 mmol) of 4-fluorophenylpiperazine, general procedure [C] and purification by preparative HPLC result in 50 mg (28% of theory) of product.

HPLC (method 1): $R_t$=4.60 min

MS (ESI-pos): m/z=528 [M+H]$^+$

Example 25A

Methyl {2-[4-(3-methoxyphenyl)piperazin-1-yl]-3-[3-(trifluoromethyl)phenyl]-3,4-dihydropyrido-[4,3-d]pyrimidin-4-yl}acetate

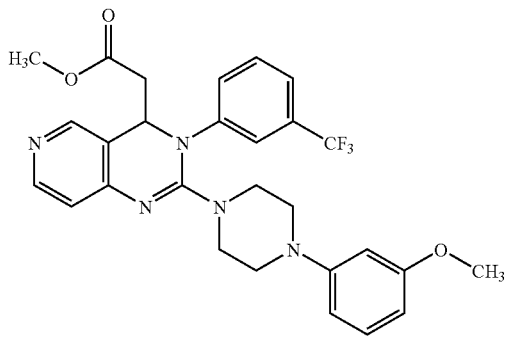

Starting from 107 mg (0.31 mmol) of the carbodiimide from Example 15A and 59 mg (0.31 mmol) of 3-methoxyphenylpiperazine, general procedure [C] and purification by preparative HPLC result in 40 mg (23% of theory) of product.

HPLC (method 1): $R_t$=4.60 min

MS (ESI-pos): m/z=540 [M+H]$^+$

Example 26A tert-Butyl {2-[4-(4-fluorophenyl)piperazin-1-yl]-3-[3-(trifluoromethyl)phenyl]-3,4-dihydropyrido-[3,2-d]pyrimidin-4-yl}acetate

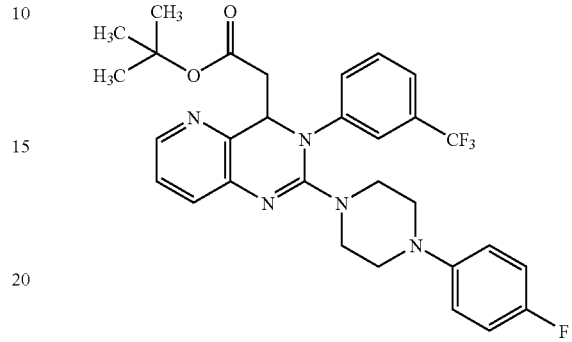

Starting from 53 mg (0.14 mmol) of the carbodiimide from Example 14A and 24 mg (0.14 mmol) of 4-fluorophenylpiperazine, general procedure [C] and purification on preparative HPLC result in 38 mg (48% of theory) of product.

HPLC (method 1): $R_t$=4.87 min

MS (ESI-pos): m/z=570 [M+H]$^+$

Example 27A

Methyl [2-[4-(4-fluorophenyl)piperazin-1-yl]-3-(2-methoxy-5-methylphenyl)-3,4-dihydropyrido-[4,3-d]pyrimidin-4-yl]acetate

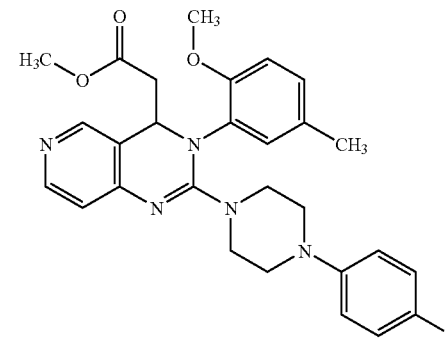

Starting from 91 mg (0.28 mmol) of the carbodiimide from Example 16A and 76 mg (0.42 mmol) of 4-fluorophenylpiperazine, general procedure [C] and purification by preparative HPLC result in 14 mg (9% of theory) of product.

HPLC (method 1): $R_t$=4.23 min

MS (ESI-pos): m/z=504 [M+H]$^+$

Example 28A

Methyl {2-[4-(4-fluorophenyl)piperazin-1-yl]-3-[2-methoxy-5-(trifluoromethyl)phenyl]-3,4-dihydropyrido[4,3-d]pyrimidin-4-yl}acetate

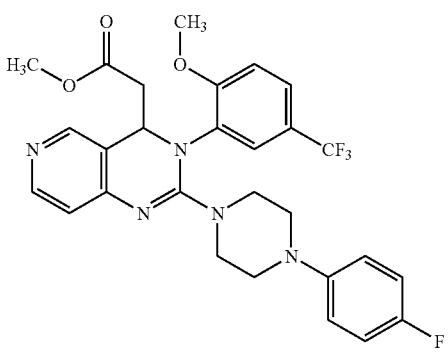

Starting from 565 mg (1.50 mmol) of the carbodiimide from Example 18A and 297 mg (1.65 mmol) of 4-fluorophenylpiperazine, general procedure [C] and purification by preparative
HPLC result in 90 mg (10% of theory) of product.
HPLC (method 1): $R_t$=4.44 min
MS (ESI-pos): m/z=558 [M+H]$^+$

Exemplary Embodiments

General Procedure [D]: Ester Hydrolysis
1.0 equivalent of the ester is dissolved in dioxane (ca. 0.5 M solution), then 3.0 equivalents of 1N sodium hydroxide solution are added, and the reaction mixture is stirred at 50° C. for 16 h. The mixture is then adjusted to pH 5 with 1N hydrochloric acid, the solvent is removed in vacuo, and the product is purified by chromatography on silica gel or preparative HPLC.

Example 1

{2-[4-(4-Fluorophenyl)piperazin-1-yl]-3-[3-(trifluoromethyl)phenyl]-3,4-dihydropyrido[3,4-d]-pyrimidin-4-yl}acetic acid hydrochloride

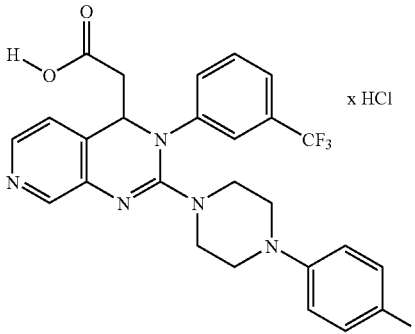

Starting from 44 mg (0.08 mmol) of the ester from Example 20A, reaction by general procedure [D] and purification by preparative HPLC result in 24 mg (52% of theory) of product.

HPLC (method 1): $R_t$=4.19 min
MS (ESI-pos): m/z=514 [M+H—HCl]$^+$
$^1$H-NMR (400 MHz, CD$_3$CN+DMSO-d$_6$): δ [ppm]=8.34 (s, 1H); 8.11 (d, 1H); 7.62 (s, 1H); 7.47 (t, 1H); 7.39-7.37 (m, 2H); 7.07 (t, 1H); 6.99 (t, 1H); 6.91-6.87 (m, 1H); 5.27-5.23 (m, 1H); 3.58-3.53 (m, 2H), further protons underneath the solvent or water signal.

Example 2

{2-[4-(3-Methylphenyl)piperazin-1-yl]-3-[3-(trifluoromethyl)phenyl]-3,4-dihydropyrido[3,4-d]-pyrimidin-4-yl}acetic acid hydrochloride

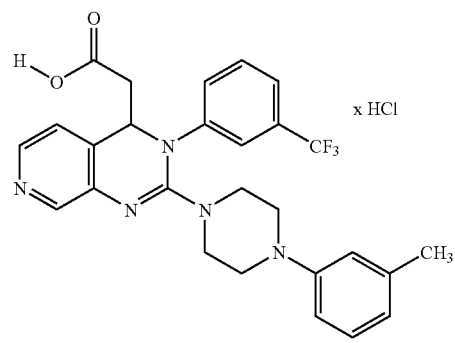

Starting from 70 mg (0.13 mmol) of the ester from Example 21A, reaction by general procedure [D] and purification by preparative HPLC result in 51 mg (71% of theory) of product.
HPLC (method 1): $R_t$=4.21 min
MS (ESI-pos): m/z=510 [M+H—HCl]$^+$
$^1$H-NMR (400 MHz, CD$_3$CN+DMSO-d$_6$): δ [ppm]=8.34 (s, 1H); 8.12 (d, 1H); 7.62 (s, 1H); 7.44 (t, 1H); 7.38-7.36 (m, 2H); 7.10 (t, 1H); 7.05 (d, 1H); 6.89-6.88 (m, 1H); 6.72-6.64 (m, 3H); 5.26-5.22 (m, 1H); 3.59-3.53 (m, 2H); 3.08-2.95 (m, 3H); 2.72-2.65 (m, 1H); 2.48-2.46 (m, 1H); 2.25 (s, 3H).

Example 3

{2-[4-(3-Chlorophenyl)piperazin-1-yl]-3-[3-(trifluoromethyl)phenyl]-3,4-dihydropyrido[3,4-d]-pyrimidin-4-yl}acetic acid hydrochloride

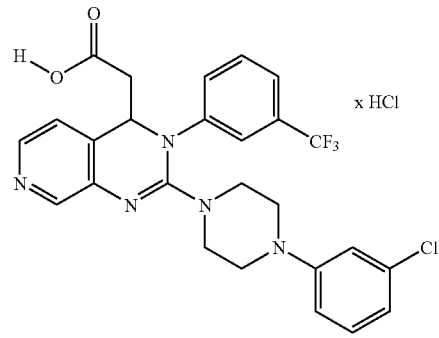

Starting from 84 mg (0.15 mmol) of the ester from Example 22A. reaction by general procedure [D] and purification by preparative HPLC result in 44 mg (52% of theory) of product.

HPLC (method 1): $R_t$=4.43 min.

MS (ESI-pos): m/z=530 [M+H—HCl]$^+$ $^1$H-NMR (400 MHz, CD$_3$CN+DMSO-d$_6$): δ [ppm]=8.34 (s, 1H); 8.12 (d, 1H); 7.62 (s, 1H); 7.46 (t, 1H); 7.39-7.35 (m, 2H); 7.19 (t, 1H); 7.05 (d, 1H); 6.89-6.88 (m, 1H); 6.83-6.79 (m, 2H); 5.26-5.22 (m, 1H); 3.59-3.53 (m, 2H); 3.13-3.02 (m, 3H); 2.72-2.65 (m, 1H); 2.48-2.41 (m, 1H).

Example 4

{2-[4-(3-Methoxyphenyl)piperazin-1-yl]-3-[3-(trifluoromethyl)phenyl]-3,4-dihydropyrido[3,4-d]-pyrimidin-4-yl}acetic acid hydrochloride

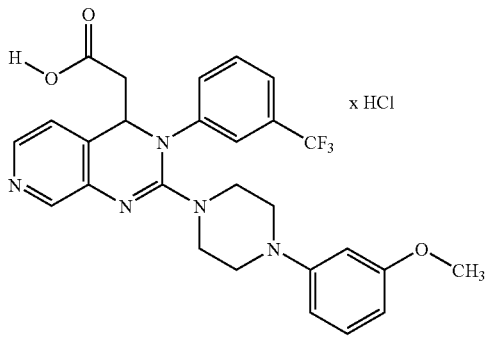

Starting from 72 mg (0.13 mmol) of the ester from Example 23A, reaction by general procedure [D] and purification by preparative HPLC result in 48 mg (67% of theory) of product.

HPLC (method 1): $R_t$=4.18 min.

MS (ESI-pos): m/z=526 [M+H—HCl]$^+$ $^1$H-NMR (400 MHz, CD$_3$CN+DMSO-d$_6$): δ [ppm]=8.35 (s, 1H); 8.12 (d, 1H); 7.56 (s, 1H); 7.46 (t, 1H); 7.39-7.36 (m, 2H); 7.12 (t, 1H); 7.05 (d, 1H); 6.50-6.47 (m, 1H); 6.43-6.39 (m, 2H); 5.26-5.22 (m, 1H); 3.73 (s, 3H); 3.59-3.52 (m, 2H); 3.09-2.98 (m, 3H); 2.72-2.65 (m, 1H); 2.48-2.46 (m, 1H).

Example 5

{2-[4-(4-Fluorophenyl)piperazin-1-yl]-3-[3-(trifluoromethyl)phenyl]-3,4-dihydropyrido[4,3-d]-pyrimidin-4-yl}acetic acid hydrochloride

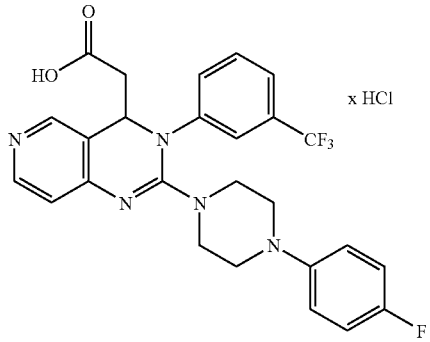

Starting from 38 mg (0.07 mmol) of the ester from Example 24A, reaction by general procedure [D] and purification by preparative HPLC result in 24 mg (67% of theory) of product.

HPLC (method 1): $R_t$=4.24 min.

MS (ESI-pos): m/z=514 [M+H—HCl]$^+$ $^1$H-NMR (400 MHz, CD$_3$CN): δ [ppm]=8.22 (d, 1H); 8.18 (s, 1H); 7.45 (s, 1H); 7.40-7.36 (m, 3H); 7.03-6.83 (m, 5H); 5.28 (t, 1H); 3.603-3.50 (m, 4H); 2.99-2.90 (m, 4H); 2.78 (dd, 1H); 2.57 (dd, 1H).

Example 6

{2-[4-(3-Methoxyphenyl)piperazin-1-yl]-3-[3-(trifluoromethyl)phenyl]-3,4-dihydropyrido[4,3-d]-pyrimidin-4-yl}acetic acid

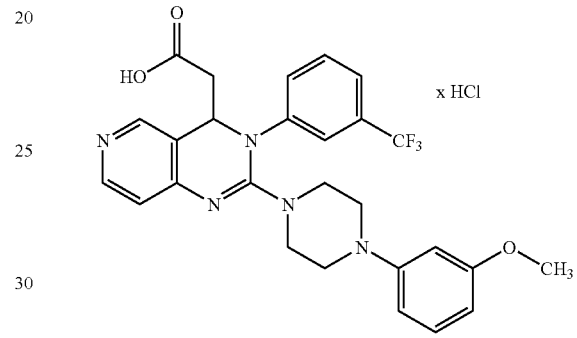

Starting from 27 mg (0.05 mmol) of the ester from Example 25A, reaction by general procedure [D] and purification by preparative HPLC result in 19 mg (72% of theory) of product.

HPLC (method 1): $R_t$=4.24 min.

MS (ESI-pos): m/z=526 [M+H—HCl]$^+$ $^1$H-NMR (400 MHz, CD$_3$CN): δ [ppm]=8.24 (d, 1H); 8.18 (s, 1H); 7.45 (s, 1H); 7.40-7.35 (m, 3H); 7.12 (t, 1H); 7.01 (d, 1H); 6.45 (d, 1H); 6.41-6.38 (m, 2H); 5.28 (t, 1H); 3.72 (s, 3H); 3.60-3.54 (m, 4H); 3.07-2.78 (m, 4H); 2.55 (dd, 2H).

Example 7

{2-[4-(4-Fluorophenyl)piperazin-1-yl]-3-[3-(trifluoromethyl)phenyl]-3,4-dihydropyrido[3,2-d]-pyrimidin-4-yl}acetic acid hydrochloride

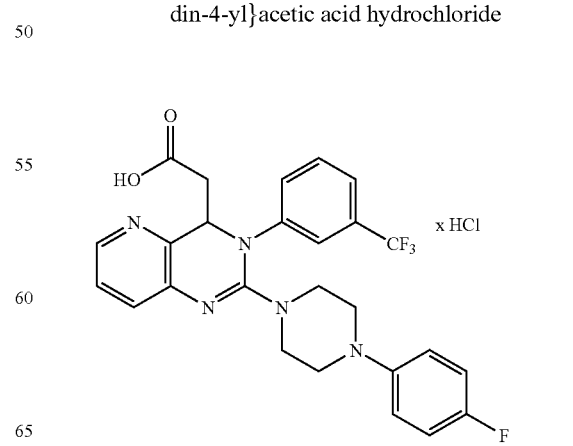

Starting from 25 mg (0.04 mmol) of the ester from Example 26A, reaction by general procedure [D] and purification by preparative HPLC result in 16 mg (66% of theory) of product.

HPLC (method 1): $R_t$=4.30 min.

MS (ESI-pos): m/z=514 [M+H—HCl]$^+$ $^1$H-NMR (400 MHz, CD$_3$CN): δ [ppm]=8.12 (d, 1H); 7.60 (s, 1H); 7.45-7.39 (m, 4H); 7.22 (dd, 1H); 6.96 (t, 2H); 6.89-6.86 (m, 2H); 5.18 (dd, 1H); 3.68-3.59 (m, 4H); 3.06-2.99 (m, 4H); 2.76 (dd, 1H); 2.63 (dd, 1H).

Example 8

[2-[4-(4-Fluorophenyl)piperazin-1-yl]-3-(2-methoxy-5-methylphenyl)-3,4-dihydropyrido[4,3-d]-pyrimidin-4-yl] acetic acid

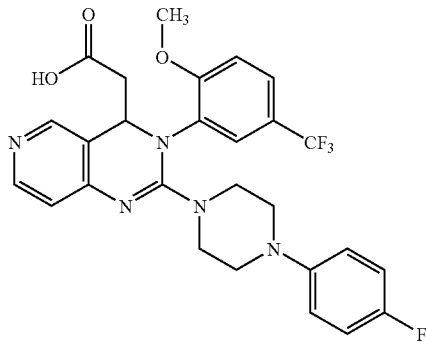

Starting from 12 mg (0.02 mmol) of the ester from Example 27A, reaction by general procedure [D] and purification by preparative HPLC result in 11 mg (97% of theory) of product.

HPLC (method 1): $R_t$=4.05 min.

MS (ESI-pos): m/z=490 [M+H]$^+$ $^1$H-NMR (400 MHz, CD$_3$CN): δ [ppm]=8.14-8.10 (m, 2H); 7.15-6.81 (m, 8H); 4.86-4.84 (m, 1H); 3.77-3.73 (m, 4H); 3.50 (s, 3H); 2.96-2.92 (m, 2H); 2.78-2.74 (m, 2H); 2.49 (dd, 1H); 2.50-2.48 (m, 1H, partly underneath CH$_3$ signal); 2.44 (s, 3H).

Example 9

{2-[4-(4-Fluorophenyl)piperazin-1-yl]-3-[2-methoxy-5-(trifluoromethyl)phenyl]-3,4-dihydro-pyrido[4,3-d]pyrimidin-4-yl}acetic acid

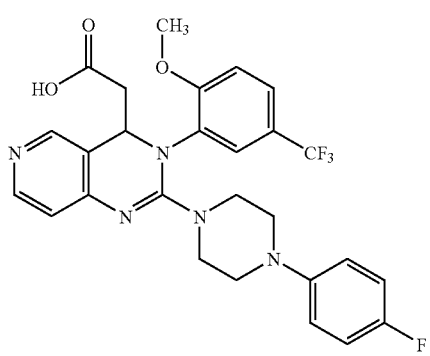

Starting from 80 mg (0.14 mmol) of the ester from Example 28A, reaction by general procedure [D] and purification by preparative HPLC result in 27 mg (35% of theory) of product.

HPLC (method 3): $R_t$=2.31 min.

MS (ESI-pos): m/z=543 [M+H]$^+$ $^1$H-NMR (400 MHz, CD$_3$CN): δ [ppm]=8.26-8.20 (m, 2H); 7.55 (d, 1H); 7.16 (d, 1H); 7.10-6.78 (m, 6H); 5.00 (dd, 1H); 3.88-3.80 (m, 4H); 3.54 (s, 3H); 3.03 (dd, 1H); 2.96-2.91 (m, 2H); 2.79-2.77 (m, 2H); 2.55 (dd, 1H).

B. ASSESSMENT OF THE PHYSIOLOGICAL ACTIVITY

The in vitro effect of the compounds of the invention can be shown in the following assays:

Anti-HCMV (Anti-Human Cytomegalovirus) Cytopathogenicity Tests

The test compounds are employed as 50 millimolar (mM) solutions in dimethyl sulphoxide (DMSO). Ganciclovir®, Foscarnet® and Cidofovir® are used as reference compounds. After addition of in each case 2 μl of the 50, 5, 0.5 and 0.05 mM DMSO stock solutions to 98 μl portions of cell culture medium in row 2 A-H for duplicate determinations, 1:2 dilutions are carried out with 50 μl portions of medium up to row 11 of the 96-well plate. The wells in rows 1 and 12 each contain 50 μl of medium. 150 μl of a suspension of 1×10$^4$ cells (human prepuce fibroblasts [NHDF]) are then pipetted into each of the wells (row 1=cell control) and, in rows 2-12, a mixture of HCMV-infected and uninfected NHDF cells (M.O.I.=0.001–0.002), i.e. 1-2 infected cells per 1000 uninfected cells. Row 12 (without substance) serves as virus control. The final test concentrations are 250-0.0005 μM. The plates are incubated at 37° C./5% CO$_2$ for 6 days, i.e. until all the cells are infected in the virus controls (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (plaque multiplier from Technomara).

The following data can be acquired from the test plates:

CC$_{50}$ (NHDF)=substance concentration in μM at which no visible cytostatic effects on the cells are evident by comparison with the untreated cell control;

EC$_{50}$ (HCMV)=substance concentration in μM which inhibits the CPE (cytopathic effect) by 50% compared with the untreated virus control;

SI (selectivity index)=CC$_{50}$ (NHDF)/EC$_{50}$ (HCMV).

Representative in vitro data for the effects of the compounds of the invention are shown in Table A:

TABLE A

| Example No. | NHDF CC$_{50}$ [μM] | HCMV EC$_{50}$ [μM] | SI HCMV |
|---|---|---|---|
| 4 | 94 | 0.2 | 470 |
| 8 | 250 | 0.14 | 1786 |
| 9 | 94 | 0.05 | 1880 |

The suitability of the compounds of the invention for the treatment of HCMV infections can be shown in the following animal model:

HCMV Xenograft Gelfoam® Model

Animals:

3-4-week old female immunodeficient mice (16-18 g), Fox Chase SCID or Fox Chase SCID-NOD or SCID beige, are purchased from commercial breeders (Taconic M+B, Jackson, USA). The animals are housed under sterile conditions (including bedding and feed) in isolators.

Virus Growing:

Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 10% foetal calf serum (FCS) with 10% DMSO at −40° C. After serial ten-fold dilutions of the virus-infected cells, the titer is determined on 24-well plates of confluent NHDF cells after vital staining with neutral red.

Preparation of the Sponges, Transplantation, Treatment and Evaluation:

Collagen sponges 1×1×1 cm in size (Gelfoam®; from Peasel & Lorey, order No. 407534; K. T. Chong et al., Abstracts of 39$^{th}$ Interscience Conference on Antimicrobial Agents and Chemotherapy, 1999, p. 439) are initially wetted with phosphate-buffered saline (PBS), the trapped air bubbles are removed by degassing, and then stored in MEM+10% FCS. 1×10$^6$ virus-infected NHDF cells (infection with HCMV Davis or HCMV AD169 M.O.I.=0.03) are detached 3 hours after infection and added in a drop of 20 µl of MEM, 10% FCS, to a moist sponge. About 16 hours later, the infected sponges are incubated with 25 µl of PBS/0.1% BSA/1 mM DTT with 5 ng/µl basic fibroblast growth factor (bFGF). For the transplantation, the immunodeficient mice are anesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue. 6 hours after the transplantation, the mice can be treated for the first time (one treatment is given on the day of the operation). On subsequent days, oral treatment with the substance is carried out three times a day (7.00 h and 14.00 h and 19.00 h), twice a day (8 h and 18 h) or once a day (14 h) over a period of 8 days. The daily dose is for example 3 or 10 or 30 or 60 or 100 mg/kg of body weight, the volume administered is 10 ml/kg of body weight. The substances are formulated in the form of a 0.5% strength Tylose suspension with 2% DMSO or a 0.5% strength Tylose suspension. 9 days after transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% foetal calf serum, 10% DMSO at −140° C. Evaluation takes place after serial ten-fold dilutions of the virus-infected cells by determining the titer on 24-well plates of confluent NHDF cells after vital staining with neutral red. The number of infected cells or infectious virus particles (infectious center assay) after the substance treatment compared with the placebo-treated control group is determined.

CYP Inhibition Assay

To investigate the mechanism-based (irreversible) inhibition of CYP3A4, the test substance is incubated in various concentrations with human liver microsomes (2 mg/ml microsomal protein) in potassium phosphate buffer of pH 7.4 with the addition of NADPH-generating system (NADP$^+$, glucose 6-phosphate and glucose-6-phosphate dehydrogenase) at 37° C. 2 aliquots are removed from the incubation at various times.

The first aliquot is incubated 1:50 in a new incubation solution (phosphate buffer, NADPH-generating system and 10 µM midazolam) at 37° C. for a further 10 min. The incubation is then stopped with acetonitrile on ice, the protein is pelleted in a centrifuge at 15 000 g, and the supernatant is analysed by standard methods of HPLC/MS for the formation of 1'-hydroxymidazolam.

The second aliquot is stopped with acetonitrile on ice and analysed by HPLC/UV/MS for remaining test substances.

Parameters typical of irreversible inhibition ($k_{inact}$, $K_i$ and partition ratio r) are determined from the two analytical data sets, and the test substance is assessed therewith (cf A. Madan, et al., in A. D. Rodrigues (ed.) "Drug-Drug Interaction" in "Drugs and the Pharmaceutical Science", Vol. 116, ISBN 0-8247-0283.2, Marcel Dekker Inc., New York, 2002.).

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of Example 1, 50 mg of lactose (monohydrate), 50 mg of corn starch (native), 10 mg of polyvinylpyrolidone (PVP 25) (from BASF, Ludwigshafen, Germany) and 2 mg of magnesium stearate.

Tablet weight 212 mg. Diameter 8 mm, radius of curvature 12 mm.

Production:

The mixture of active ingredient, lactose and starch is granulated with a 5% strength solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:

Composition:

1000 mg of the compound of Example 1, 1000 mg of ethanol (96%), 400 mg of Rhodigel (xanthan gum from FMC, Pa., USA) and 99 g of water.

10 ml of oral suspension are equivalent to a single dose of 100 mg of the compound of the invention.

Production:

The Rhodigel is suspended in ethanol, and the active ingredient is added to the suspension. The water is added while stirring. The mixture is stirred for about 6 h until the swelling of the Rhodigel is complete.

Solution which can be Administered Intravenously:

Composition:

10-500 mg of the compound of Example 1, 15 g of polyethylene glycol 400 and 250 g of water for injections.

Production:

The compound of Example 1 is dissolved together with polyethylene glycol 400 in the water with stirring. The solution is sterilized by filtration (pore diameter 0.22 µm) and dispensed under aseptic conditions into heat-sterilized infusion bottles. The latter are closed with infusion stoppers and crimped caps.

The invention claimed is:

1. A compound of the formula (I)

in which
  Ar is aryl, in which aryl may be substituted by 1 to 3 substituents, where the substituents are selected independently of one another from the group consisting of alkyl, alkoxy, formyl, hydroxycarbonyl, alkylcarbonyl, alkoxycarbonyl, trifluoromethyl, halogen, cyano, hydroxy, amino, alkylamino, aminocarbonyl and nitro,
    in which alkyl may be substituted by 1 to 3 substituents, where the substituents are selected independently of one another from the group consisting of halogen, amino, alkylamino, hydroxy and aryl,
    or two of the substituents on the aryl form together with the carbon atoms to which they are bonded a 1,3-dioxolane, a cyclopentane ring or a cyclohexane ring, and the optionally present third substituent is selected independently thereof from the group consisting of alkyl, alkoxy, formyl, hydroxycarbonyl, alkylcarbonyl, alkoxycarbonyl, trifluoromethyl, halogen, cyano, hydroxy, amino, alkylamino, aminocarbonyl and nitro,
  $Q^1$, $Q^2$, $Q^3$ and $Q^4$ are CH or N,
    where exactly one of $Q^1$, $Q^2$, $Q^3$ and $Q^4$ are N and the others are simultaneously CH,
  $R^1$ is hydrogen, amino, alkyl, alkoxy, alkylamino, alkylthio, cyano, halogen, nitro or trifluoromethyl,
  $R^2$ is hydrogen, alkyl, alkoxy, alkylthio, cyano, halogen, nitro or trifluoromethyl,
  $R^3$ is amino, alkyl, alkoxy, alkylamino, alkylthio, cyano, halogen, nitro, trifluoromethyl, alkylsulphonyl or alkylaminosulphonyl,
or
  one of the radicals $R^1$, $R^2$ and $R^3$ is hydrogen, alkyl, alkoxy, cyano, halogen, nitro or trifluoromethyl, and the other two form together with the carbon atoms to which they are bonded a 1,3-dioxolane, a cyclopentane ring or a cyclohexane ring,
  $R^4$ is hydrogen or alkyl,
  $R^5$ is hydrogen or alkyl,
or
  the radicals $R^4$ and $R^5$ in the piperazine ring are bonded to exactly opposite carbon atoms and form a methylene bridge optionally substituted by 1 to 2 methyl groups,
  $R^6$ is hydrogen, alkyl, alkoxy, alkylthio, formyl, hydroxycarbonyl, aminocarbonyl, alkylcarbonyl, alkoxycarbonyl, trifluoromethyl, halogen, cyano, hydroxy or nitro,
and
  $R^7$ is hydrogen, alkyl, alkoxy, alkylthio, formyl, hydroxycarbonyl, alkylcarbonyl, alkoxycarbonyl, trifluoromethyl, halogen, cyano, hydroxy or nitro,
or a salt-thereof.

2. The compound according to claim 1, characterized in that
  Ar is phenyl, in which phenyl may be substituted by 1 to 3 substituents, where the substituents are selected independently of one another from the group consisting of $C_1$-$C_6$-alkyl, $C_1$-$C_6$-alkoxy, hydroxycarbonyl, $C_1$-$C_6$-alkylcarbonyl, $C_1$-$C_6$-alkoxycarbonyl, trifluoromethyl, fluorine, chlorine, bromine, cyano, hydroxy, amino, $C_1$-$C_6$-alkylamino and nitro,
    or two of the substituents on the phenyl form together with the carbon atoms to which they are bonded a 1,3-dioxolane, and the optionally present third substituent is selected independently thereof from the group consisting of alkyl, alkoxy, formyl, hydroxycarbonyl, alkylcarbonyl, alkoxycarbonyl, trifluoromethyl, halogen, cyano, hydroxy, amino, alkylamino, aminocarbonyl and nitro,
  $Q^1$, $Q^2$ and $Q^3$ are CH or N,
    where always exactly one of $Q^1$, $Q^2$ and $Q^3$ is N and the others are simultaneously CH,
  $Q^4$ is CH,
  $R^1$ is hydrogen, $C_1$-$C_3$-alkyl, $C_1$-$C_3$-alkoxy, $C_1$-$C_3$-alkylthio, fluorine or chlorine,
  $R^2$ is hydrogen, $C_1$-$C_3$-alkyl, $C_1$-$C_3$-alkoxy, $C_1$-$C_3$-alkylthio, fluorine or chlorine,
  $R^3$ is $C_1$-$C_4$-alkyl, cyano, fluorine, chlorine, nitro, trifluoromethyl or $C_1$-$C_3$-alkylsulphonyl,
or
  one of the radicals $R^1$, $R^2$ and $R^3$ is hydrogen, $C_1$-$C_3$-alkyl, $C_1$-$C_3$-alkoxy, cyano, halogen, nitro or trifluoromethyl, and the other two form together with the carbon atoms to which they are bonded a cyclopentane ring or a cyclohexane ring,
  $R^4$ is hydrogen or methyl,
  $R^5$ is hydrogen,
  $R^6$ is hydrogen, $C_1$-$C_3$-alkyl, $C_1$-$C_3$-alkoxy, hydroxycarbonyl, aminocarbonyl, trifluoromethyl, fluorine, chlorine, cyano, hydroxy or nitro,
and
  $R^7$ is hydrogen, $C_1$-$C_3$-alkyl, $C_1$-$C_3$-alkoxy, fluorine, chlorine, cyano or hydroxy.

3. The compound according to claim 1 or 2, characterized in that
  Ar is phenyl, in which phenyl may be substituted by 1 to 2 substituents, where the substituents are selected independently of one another from the group consisting of methyl, methoxy, fluorine and chlorine,
  $Q_1$, $Q_2$ and $Q_3$ are CH or N,
    where always exactly one of $Q_1$, $Q_2$ and $Q_3$ is N, and the others are simultaneously CH,
  $Q^4$ is CH,
  $R^1$ is hydrogen, methyl or methoxy, methylthio, fluorine or chlorine,
  $R^2$ is hydrogen,
  $R^3$ is methyl, isopropyl, tert-butyl, cyano, fluorine chlorine, nitro or trifluoromethyl,
  $R^4$ is hydrogen,
  $R^5$ is hydrogen,
  $R^6$ is hydrogen, aminocarbonyl, fluorine, chlorine, cyano or hydroxy,
and
  $R^7$ is hydrogen.

4. The compound according to claim 1 or 2, characterized in that
  Ar is phenyl, in which phenyl may be substituted by 1 to 2 substituents, where the substituents are selected independently of one another from the group consisting of methyl, methoxy, fluorine and chlorine, $Q^1$, $Q^2$ and $Q^3$ are CH or N, where always exactly one of $Q^1$, $Q^2$ and $Q^3$ is N, and the others are simultaneously CH, $Q^4$ is CH, $R^1$ is hydrogen, methyl or methoxy, $R^2$ is hydrogen, $R^3$ is methyl, tert-butyl, chlorine or trifluoromethyl, $R^4$ is hydrogen, $R^5$ is hydrogen, $R^6$ is hydrogen and $R^7$ is hydrogen.

5. A pharmaceutical composition comprising a compound according to any of claims 1 to 4 in combination with an inert, non-toxic, pharmaceutically suitable excipient.

* * * * *